(12) United States Patent
Howard

(10) Patent No.: US 10,104,344 B2
(45) Date of Patent: Oct. 16, 2018

(54) REMOTE SCANNING AND DETECTION APPARATUS AND METHOD

(71) Applicant: GS ENGINEERING SERVICES, INC., Houghton, MI (US)

(72) Inventor: Gary Bryan Howard, Smithfield, UT (US)

(73) Assignee: GS ENGINEERING SERVICES, INC., Houghton, MI (US)

( * ) Notice: Subject to any disclaimer, the term of this patent is extended or adjusted under 35 U.S.C. 154(b) by 218 days.

(21) Appl. No.: 14/708,428

(22) Filed: May 11, 2015

(65) Prior Publication Data

US 2015/0330911 A1 Nov. 19, 2015

Related U.S. Application Data

(60) Provisional application No. 61/992,472, filed on May 13, 2014.

(51) Int. Cl.

| G01N 33/42 | (2006.01) |
|---|---|
| H04N 7/18 | (2006.01) |
| H04N 5/33 | (2006.01) |
| B60R 1/00 | (2006.01) |
| G01N 21/88 | (2006.01) |
| G01N 25/72 | (2006.01) |

(52) U.S. Cl.
CPC ............... *H04N 7/183* (2013.01); *B60R 1/00* (2013.01); *G01N 21/8803* (2013.01); *G01N 33/42* (2013.01); *H04N 5/33* (2013.01); *H04N 7/181* (2013.01); *B60R 2300/105* (2013.01); *G01N 21/8851* (2013.01); *G01N 25/72* (2013.01)

(58) Field of Classification Search
CPC ......... G08G 1/00; G01B 11/02; G01S 7/4817; G01S 13/885; G01S 2013/9357; G06K 9/00798; G01N 21/8803; G01N 21/8851; G01N 25/72; G01N 33/42
See application file for complete search history.

(56) References Cited

U.S. PATENT DOCUMENTS

| 4,690,553 A | 9/1987 | Fukamizu et al. |
|---|---|---|
| 4,910,592 A | 3/1990 | Shroy, Jr. et al. |
| 4,910,593 A * | 3/1990 | Weil ...................... G01V 9/005 348/164 |
| 5,790,243 A * | 8/1998 | Herr ...................... G01B 11/24 356/2 |
| 7,697,727 B2 * | 4/2010 | Xu ...................... G01C 11/025 382/108 |
| 8,803,977 B2 | 8/2014 | Uchima et al. |
| 2006/0061485 A1 | 3/2006 | Doherty et al. |
| 2012/0173150 A1 | 7/2012 | Romero et al. |
| 2012/0218411 A1 | 8/2012 | Wu et al. |
| 2013/0176424 A1 | 7/2013 | Weil |
| 2014/0368373 A1 | 12/2014 | Crain et al. |
| 2015/0330911 A1 | 11/2015 | Howard |

* cited by examiner

*Primary Examiner* — Obafemi Sosanya
(74) *Attorney, Agent, or Firm* — Brooks Kushman P.C.

(57) ABSTRACT

A surface scanning method and apparatus attached to a highway vehicle, mobile equipment, or the like, that traverses existing roadways and bridges. The apparatus has at least one of a variously adaptable, complete, and ready to operate packaged kit including configured sensor suites with one or more of a visual scanning sensor; an infra-red scanning sensor; and an elevation measuring sensor.

11 Claims, 2 Drawing Sheets

REMOTE SCANNING AND DETECTION APPARATUS AND METHOD

CROSS-REFERENCE TO RELATED APPLICATIONS

This application claims the benefit of U.S. provisional patent application Ser. No. 61/992,472 filed May 13, 2014.

BACKGROUND OF THE INVENTION

(1) Field of the Invention

Disclosed herein are an apparatus and method for accurate infrared and visible spectrum scanning of an underlying terrain, defect detection, high speed integration and data processing of roadway and bridge subsurface and surface defects at normal highway speeds.

(2) Description of Related Art

Substantial effort, human resources, and funds are expended on a world-wide basis related to the natural and constant deterioration of roadways, bridge decks, and highway infrastructure. In particular, road surface materials such as asphalt, concrete, and reinforced concrete used for bridge decks and roadways are continuously being subject to degradation due to environmental exposure, wear, and mechanical damage caused by vehicle traffic. The constant degradation of surface materials is further enhanced by regional circumstances including and not limited to normal seasonal climatic cycles, various types of weather, high concentrations of salt-sea air in coastal areas, and exposure to de-icing salts, chlorides and developing types of de-icing chemicals in more temperate regions.

Timely, consistent and comprehensive roadway and bridge infrastructure inspection and assessment is of high importance as it relates to early detection and quantification of various types of deterioration. Without the ability to rapidly and consistently monitor the rates at which roadway and bridge deck surface material is degrading, the likelihood of further accelerated deterioration, without properly applied service and maintenance to avoid such trends, will tend to cause even further accelerated rates of deterioration.

Various methods of infrastructure inspection and assessment have been developed. Known methods range from simple visual inspection to highly complex methods that utilize various tools and electronic devices. One traditional method involves mechanically dragging heavy steel chain across a roadway or bridge deck surface by hand.

The road surface material is typically concrete in this case, and any changes in the sound that the chain produces as it is dragged along the surface is carefully marked and noted as to the particular locations and areas on the surface itself. Particular changes to the sound produced by the chain may suggest underlying material or structural defects such as, for example, structural cracks or areas of hidden delamination within the concrete. Other mechanical means related to sounding techniques also have been developed and used with varying degrees of success.

Accordingly, the costs and resources required to alleviate and correct such rapidly accelerating rates of deterioration will increase and accelerate in like fashion. Further, the effects of roadway and bridge deck deterioration, if left to remain unchecked, will continue to trend toward the compromised safety of motorists and vehicles. This aspect brings about an even greater sense of urgency with this issue.

Among the references considered before filing this application are: U.S. patent publication documents 2012/0173150; 2012/0218411; 2013/0176424 and U.S. Pat. Nos. 8,803,977; 7,697,727; and 4,910,592.

BRIEF SUMMARY OF THE INVENTION

Disclosed herein are an apparatus, system and method for scanning and scoping inspection, analysis, location and quantification of defects of numerous types of transportation surfaces and other structures. Several aspects of this disclosure relate to the use of a vehicle-mounted infrared data capture camera, a high definition visible band camera, and a laser distance or range finder that allows continuous elevation measurement of the height of the respective cameras above the surface being scanned. Additionally, the system is integrated with GPS hardware to ensure synergistic timing between image collection and geographic positioning. In one embodiment data from sensors associated with the vehicle-mounted devices are acquired simultaneously with a time stamp and a location stamp for accurate data fusion and correlation.

For example, the methodology disclosed is suitable for scanning and scoping of airport runways and taxiways since it is mounted on commercially available highway vehicles. Applications of the disclosed method and apparatus extend to infrastructure analysis within the aviation industry including, for example, commercial, private, and military airports and facilities. The disclosed techniques can be utilized in connection with virtually any type of transportation surface and/or infrastructure.

The self-contained system apparatus configurations include variously selected and predesigned components. Once configured and assembled as a prepackaged sensor suite as installation kits, the components are readily adaptable to commercially available highway vehicles for inspection and evaluation of roadways, bridge decks, sub-surface and surface defects, and related transportation infrastructures. Preferably, the disclosed techniques are optionally coupled with preferably standardized and adopted federal and state departments of transportation (DOT) output analysis and reporting of the results.

The present invention provides an improved road surface and subsurface defects scanning and scoping apparatus, system, and method that is adaptable to virtually any commercially available highway vehicle, mobile equipment, or the like, for the purposes of accurate and rapid collection and recording of surface infrared and visible spectrum image data at nominal highway speeds.

The present invention also provides significantly improved accuracy, rapid on-site integration, and rapid processing of the recorded scan data and high-definition visible band imagery. The disclosed techniques enable the operator to identify material defects in concrete roadways and bridge decks, since areas of delamination, previous patch repairs, spalling and other defects are readily identified by infrared camera data. The operator can quickly identify and reconcile defects and anomalies presented by the infrared camera data with the high-definition visible band imagery. Once the reconciliatory steps are complete, software provides accurate correlation and orientation of the recorded data with respect to global positioning system (GPS) coordinates and the time stamp.

Outputs from the techniques disclosed include correlation with geographic information systems (GIS) as well as KLM file formats associated with GIS service providers such as, and not limited to for example, United States Geological Survey (USGS), or Google Earth, thus providing accurate reference to these types of three-dimensional databases.

As noted earlier, the present invention accurately and quickly identifies and quantifies various types of structural defects within roadway and bridge deck surfacing materials such as concrete and asphalt at normal and nominal traffic highway speeds. Therefore, the road surface and substructure scanning and scoping apparatus, system, and method reduces or eliminates road and traffic lane closures associated with prior methods.

These and other features, advantages, and objects of the present invention will be further understood and appreciated by those skilled in the art by reference to the following specification, claims, and appended drawings.

DETAILED DESCRIPTION OF THE INVENTION

Figure 1:
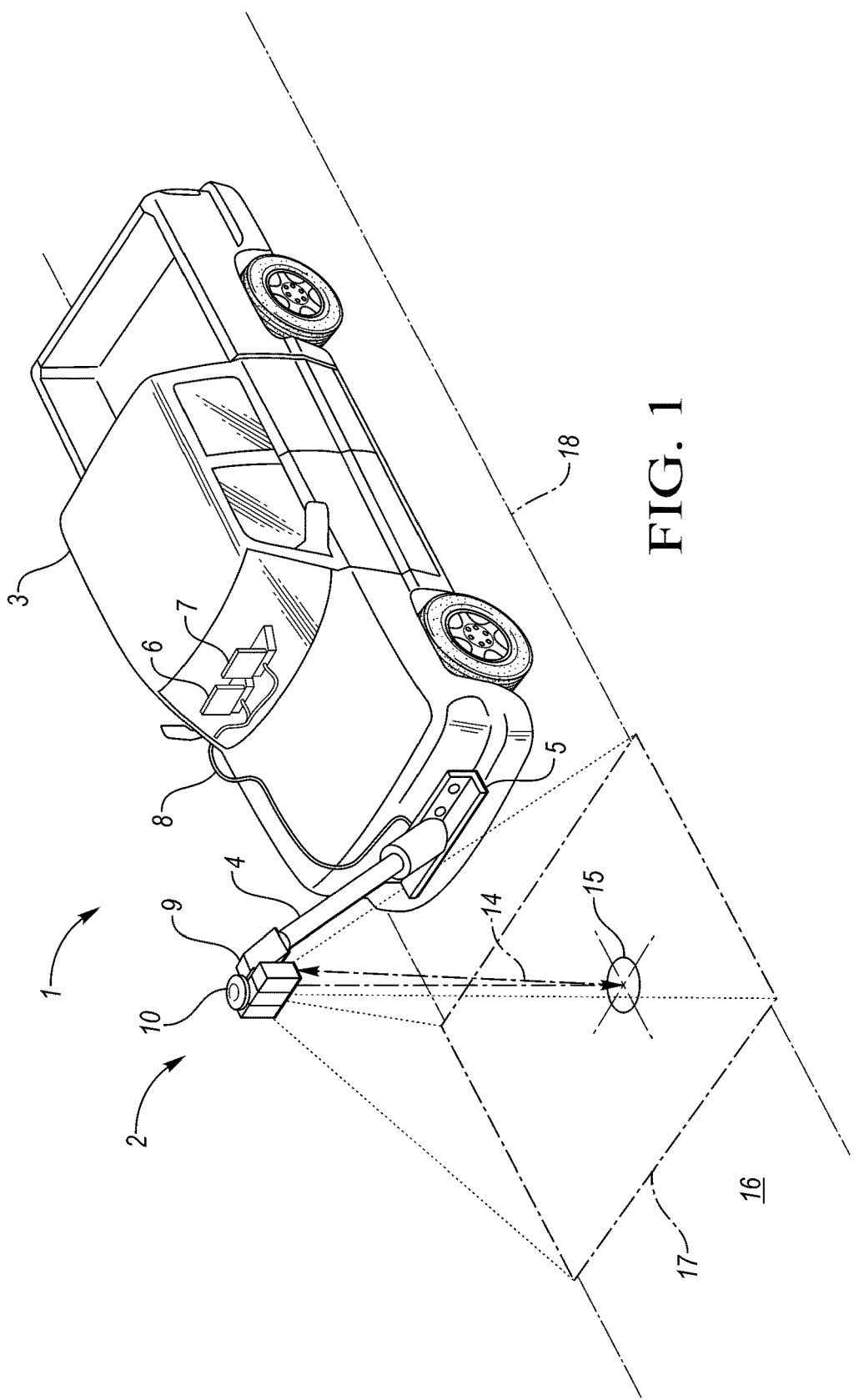
FIG. 1 is an overall left front perspective view of roadway and bridge deck scanning and scoping apparatus and system embodying several features of the present invention.

FIG. 1 depicts a roadway and bridge deck scanning and scoping apparatus and system embodying some features of the present invention—a scanning and scoping sensor head assembly adaptably mounted to a commercially available highway vehicle by a structural boom assembly. The boom assembly is attached to and preferably forwardly-mounted on the vehicle by attachable brackets. The scanning and scoping sensors are directed generally vertically and downwardly at the roadway or bridge deck surface to be scanned and scoped to prevent skewing of the edges of the frames as the vehicle is driven while it travels forwardly at nominal highway speeds thereabove for recording electronic signal data from the sensors.

Figure 2:
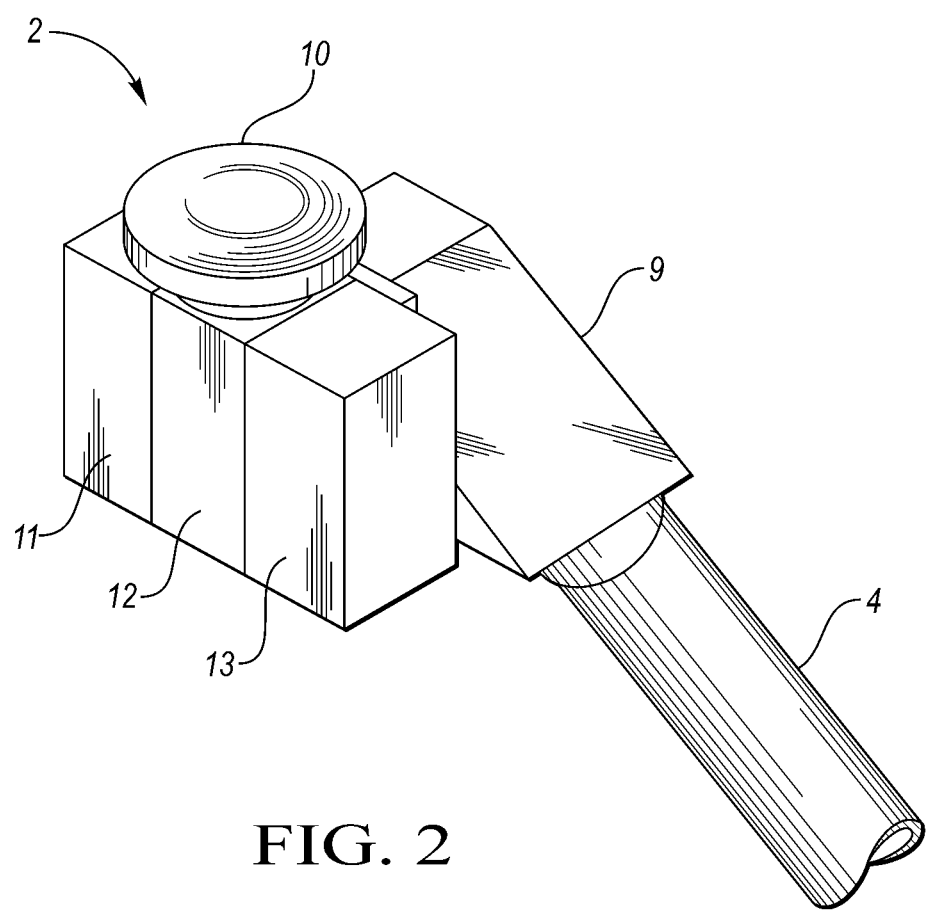
FIG. 2 is an enlarged left front perspective view of the scanning and scoping head assembly of the present invention.

FIG. 2 is a left front perspective view of one embodiment of the scanning and scoping head assembly of the present invention. It shows the general arrangement of at least four different types of sensors— a. a high-definition visual band camera for capturing images of the surface to be evaluated, b. a high-definition infrared camera for sub-surface observation, c. a laser range finder for accurately measuring the actual working height or elevation of the scanning and scoping head assembly above the roadway or bridge deck surface to be scanned, and d. a global positioning system (GPS) antenna preferably mounted at the upper portion of the scanning and scoping head assembly. The GPS locates the scanning and scoping head assembly as it remains either stationary or travels with respect to latitude, longitude and elevation (three dimension coordinates) within GPS measurement networks and geographic information systems (GIS).

The disclosed apparatus and method enable accurate and repeatable infrared and visible spectrum scanning. This allows surface and sub-surface conditions to be sensed and reported to an on-board processor. Information about roadway and bridge deck sub-structures and surface defects can be integrated and processed while the vehicle moves at normal highway speeds. Linked to or embedded within the processor is a preferably standardized and accepted DOT output analysis and method for reporting the results. More particularly, the present invention provides for a variety of generally self-contained system apparatus configurations.

The invention accurately, quickly, and reliably locates, identifies and quantifies the structural conditions and integrity of the structural materials underlying the surfaces and sub-surface structures being scanned.

A representative arrangement is shown in FIG. 1. System 1 provides accurate and repeatable infrared and visible spectrum scanning, detection, high-speed integration and data processing of roadway and bridge deck substructures and surface defects at normal highway speeds. The system 1 optionally includes a scanning and scoping sensor head assembly 2 adaptably mounted to a commercially available highway vehicle 3 by a structural boom assembly 4. The structural boom assembly 4 is attached to and is forwardly mounted to the vehicle by brackets 5 that support the sensor head assembly 2 above the surface 16 to be scanned and scoped.

In this embodiment of the invention the structural boom assembly 4 is preferably attached to the forward end of vehicle 3 to mechanically support the sensor head assembly 2 above the surface to be scanned 16. It is however understood that the boom assembly 4 may optionally be adapted and attached to the rear portion of the vehicle 3. Alternatively, the boom assembly can be attached to either the left or right side portions of the vehicle 3 as may be preferred. Similarly, the sensor head assembly 2 can be mounted at alternate locations with respect to the vehicle 3, the desired direction of travel of the vehicle 3, or area to be scanned.

Bracket assembly 9 adapts and rigidly mounts the sensor head assembly 2 to the boom assembly 4. When not in use the scanning and scoping sensor head assembly 2, boom assembly 4, bracket assembly 9, attachable brackets 5 and electronic signal cable 8 may be readily detached and otherwise disassembled from the vehicle 3 to allow normal operational use and utility of the vehicle 3 as desired.

In one embodiment, the scanning and scoping sensor head assembly 2 has three scanning and scoping sensors 11, 12, and 13. Scanning sensor 11 comprises a visual band high-definition video camera. The camera is oriented generally vertically and receives visible band video images of the surface to be scanned 16 at scanned area 17. During this operation, the highway vehicle 3 may remain stationary or be driven forwardly.

Scanning sensor 12 typically is a high-definition infrared camera that is oriented vertically. It receives infrared video images of the surface to be scanned 16 at scanned area 17 as the highway vehicle 3 remains stationary or is driven forwardly.

A distance measuring sensor 13 may, for example, include a laser range finder, a sonic distance measuring sensor, or other similar sensors having non-contact distance measuring capability. Distance measuring sensor 13 is disposed generally adjacent to both the visible band camera 11 and infrared camera 12 and is preferably calibrated to match the elevation of both the visible band camera 11 and the infrared camera 12.

The distance measuring sensor 13 emits, for example in the case of a laser range finder a laser beam 14 onto the surface being scanned 17 at target area 15. Laser beam 14 is then reflected back to the sensing portion of laser range finder 13. The received signal is then processed electronically to provide an accurate real-time elevation distance or height measurement of the sensor head assembly 2 above the surface 16 to be scanned and scoped.

Electronic output signals generated by the visible camera 11, infrared camera 12, and distance measuring sensor 13 are transmitted to a computer processor 7 by electrical sensor and control wiring cable 8. Computer processor 7 is preferably mounted for operator access inside the passenger compartment 19 of vehicle 3. The respective signals are processed and incorporated as data signals for use by software programs that run on or in conjunction with the computer processor 7.

The scanning and scoping sensor head assembly 2 also has a GPS sensor antenna 10 as shown in both FIGS. 1 and 2. The GPS sensor antenna 10 is mounted preferably at the uppermost portion of the sensor head assembly 2. In this way, it may clearly receive signals from GPS satellites and other similar position tracking systems. Electronic output signals generated by the GPS sensor antenna 10 are transmitted to the same computer processor or a different computer processor 6 by electrical sensor and control wiring cable 8.

For example, the disclosed methodology enables the scanning and scoping of airport runways and taxiways. Applications extend to infrastructure analysis within other facets of the aviation industry including, for example, commercial, private, and military airports and facilities and to virtually any type of transportation surface and/or infrastructure.

In use, embodiments of the disclosed system include selected and pre-designed components. Once configured and assembled they may be offered as prepackaged sensor suite installation kits that are readily adaptable to commercially available highway vehicles for inspection and evaluation of roadways, bridge decks, sub surface, surface defects, and related transportation infrastructures. Optionally the disclosed methodology may be used in combination with preferably standardized and adopted federal and state Departments of Transportation (DOT) systems for output analysis and reporting of the results.

The present invention provides significantly improved accuracy, rapid on-site integration, and rapid processing of the recorded scan data and high-definition visible band imagery. It provides the operator with the ability to identify material defects in concrete roadways and bridge decks whereby the presence of areas of delamination, previous patch repairs, spalling, and other defects are readily identified by means of infrared camera data.

The present invention also provides the operator with the ability to quickly identify and reconcile defects and anomalies presented by the infrared camera data with the high-definition visible band imagery. Once the reconciliatory steps are complete, software may be utilized to provide accurate correlation and orientation of the recorded data with respect to global positioning system (GPS) coordinates.

The present invention is therefore adapted to provide output reporting including correlation with geographic information systems (GIS) as well as KLM file formats associated with GIS service providers such as, and not limited to for example, United States Geological Survey (USGS), or Google Earth, thus providing accurate reference to these types of 3-dimensional databases.

The present invention accurately and quickly identifies and quantifies various types of structural defects within roadway and bridge deck surfacing materials such as concrete and asphalt while the vehicular platform moves at normal and nominal traffic highway speeds. Therefore, the road surface and substructure scanning and scoping apparatus, system, and method reduces or eliminates road and traffic lane closures associated with prior methods.

In a nutshell, disclosed herein is a surface scanning apparatus that is supported by a commercially available highway vehicle, mobile equipment, or the like. The apparatus can be moved along and be readily operated upon exiting roadways and bridges. It includes at least one member of a suite of sensors that make up a variously adaptable, complete, and ready to operate packaged kit.

As mentioned earlier, the surface scanning apparatus can be operated at nominal highway speeds and preferably at a general magnitude of travel velocity in the range of 50 miles per hour (80 kilometers per hour). In this way, roadway lane and bridge closures, the re-routing of traffic onto alternate routes, the slowing of normal vehicle traffic, or otherwise significant interruptions to the normal and safe flow of traffic and vehicles are at least partially or entirely eliminated.

In one exemplary embodiment, the surface scanning apparatus system and kit has a vehicle-mounted high-definition visible band camera; a vehicle mounted high-definition infrared band camera; a structural boom assembly attached to the highway vehicle so that the high-definition visible and infrared cameras are remotely mounted at a desired elevation above the surface to be scanned to achieve a desired field of view (FOV); and a GPS mounted alongside or thereabove. The field of view (FOV) to be scanned may be selected and preferably for example be approximately at least one traffic lane in width or more as a portion of the roadway or bridge deck surface.

Preferably, the structural boom assembly also supports an electronic laser range finder for accurately measuring the elevation height of the vehicle-mounted high-definition visible and infrared band cameras. The electronic laser range finder provides an accurate reference signal for calibration and correction factors related to the elevation height and data signals received by the vehicle-mounted high-definition visible and infrared band cameras.

As mentioned, there are one or more GPS antennas for real-time recording of vehicle position, speed, and direction with respect to actual latitude and longitude coordinates (GIS and KLM files associated with Google Earth). Such signals further correlate these measurements with the measurements and data collected by the vehicle-mounted high-definition visible and infrared band cameras.

Coupled with these components are one or more computer processors for digitally processing the measurements and video data signals collected by the vehicle-mounted high-definition visible and infrared band cameras. The computer processors have a high-speed processor and software for rapid integration (fast high speed frame rate) of video data signals collected by the vehicle-mounted high-definition visible and infrared band cameras. In communication with the processor(s) is a digital storage device whereby recorded data and signal outputs from the means described above are stored.

Also provided are digital proprietary software programs that process the recorded data and signal outputs and formats it for output and analysis.

Optionally available is at least one digital output monitor for displaying the output of the digital proprietary software such that the operator may readily visualize the internal structural condition of the material below the surfaces scanned. This allows the operator to identify and locate structural defects and features apart from those caused by superficial, visible band, or nonstructural defects of the scanned surfaces.

Preferably, the output format includes quantitative data related to the calculated percentage of structural defects and their respectively defined physical locations with respect to GPS standards in accordance with customer defined specifications, the transportation industry, and respective governing body standards.

The disclosed infrared and visible surface scanning and scoping apparatus, system, and method are adaptable to any commercially available highway vehicle, mobile equipment, or the like for accurate and rapid collection of surface image data, processing, and analysis reporting.

One way to practice the disclosed techniques is to provide, not necessarily in the order listed:

a vehicle-mounted high-definition visible band camera;

a vehicle-mounted high-definition infrared band camera;

a structural boom assembly attached to the vehicle whereby the high-definition visible and infrared cameras are remotely mounted at a desired elevation height above the surface to be scanned so as to encompass the desired field of view (FOV) (the FOV is preferably for example approximately at least one traffic lane in width or more as a portion of the roadway or bridge deck surface);

an electronic laser range finder for accurately measuring the elevation height of the vehicle-mounted high-definition visible and infrared band cameras (the electronic laser range finder provides an accurate reference signal for calibration and correction factors related to the elevation height and data signals received by the vehicle-mounted high-definition visible and infrared band cameras);

at least one GPS antenna for real-time recording of vehicle position, speed, and direction with respect to actual latitude and longitude coordinates (GIS and KLM files associated with Google Earth), further correlating these measurements to the measurements and data collected by the vehicle-mounted high-definition visible and infrared band cameras;

a computer for digitally processing the measurements and video data signals collected by the vehicle-mounted high-definition visible and infrared band cameras (optionally, the computer also runs software for rapid integration—fast high speed frame rate—of video data signals collected by the vehicle-mounted high-definition visible and infrared band cameras; and has (1) a digital storage device whereby recorded data and signal outputs from the means described above are stored; (2) digital proprietary software programs that further process the recorded data and signal outputs and formats the results for output and analysis; and (3) at least one digital output monitor that displays the output of the digital proprietary software so the operator may readily visualize the internal structural condition of the material below the surfaces previously scanned—this allows the operator to identify and locate structural defects and features apart from those cause by superficial, visible band, or non-structural defects of the scanned surfaces.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A surface and sub-surface scanning apparatus attachable to a highway vehicle, mobile equipment, or the like, that traverses a structure to be evaluated, the apparatus including at least one of a variously adaptable, and ready to operate packaged kit including a detachable and adjustable structural boom assembly that supports configured sensor suites with one or more of a visual scanning sensor, an infra-red scanning sensor, at least one GPS antenna and an elevation measuring sensor, wherein the visual scanning sensor comprises a high-definition visible band camera for capturing surface images of the structure to be evaluated;

the infra-red scanning sensor comprises a high-definition infrared band camera for sub-surface observation;

the at least one GPS antenna enables real-time recording of vehicle position, speed, and direction with respect to actual position coordinates and ensures synergistic timing between image collection and geographic positioning;

the structural boom assembly is attachable to a front, a rear or a side of the vehicle, thus enabling the high-definition visible band camera and infrared scanning sensor to be mounted at a desired elevation above the structure to be scanned to achieve a desired field of view (FOV), the field of view (FOV) being preferably approximately at least one traffic lane in width; and the elevation measuring sensor comprises an electronic laser range finder for measuring the height of the high-definition visible band camera and scanning sensor above the structure to be scanned, the electronic laser range finder providing a reference signal for calibration and correction factors related to the height and data signals received by the high-definition infrared band camera and visible band camera.

2. The surface and sub-surface scanning apparatus of claim 1, wherein the vehicle operates at nominal highway speeds and preferably at a general magnitude of travel velocity in the range of 50 miles per hour (80 kilometers per hour), whereby roadway lane and bridge closures, the re-routing of traffic onto alternate routes, the slowing of normal vehicle traffic, or otherwise significant interruptions to the normal and safe flow of traffic and vehicles are at least partially or entirely eliminated.

3. The surface and sub-surface scanning apparatus of claim 1, wherein the visual scanning sensor, the intra-red scanning sensor, or both, scan perpendicularly in relation to the structure to be scanned.

4. The surface and sub-surface scanning apparatus of claim 1, also including a computer for processing measurements and video data signals collected by the vehicle-mounted high-definition visible and infrared band cameras.

5. The surface and sub-surface scanning apparatus of claim 4, wherein the computer further includes a high-speed processor and software for rapid integration of video data signals collected by the vehicle-mounted high-definition visible and infrared band cameras.

6. The surface and sub-surface scanning apparatus of claim 5, wherein the computer and high-speed processor further include a digital storage device whereby recorded data and signal outputs are stored.

7. The surface and sub-surface scanning apparatus of claim 6, wherein the computer and high-speed processor further include software programs whereby the recorded data and signal outputs are further processed and formatted for output and analysis.

8. The surface and sub-surface scanning apparatus of claim 7, wherein the scanning apparatus and kit further include at least one output monitor for displaying output information so that the operator may visualize an internal structural condition of material below the surface scanned, thus allowing the operator to identify and locate structural defects and features apart from those representative of superficial, or nonstructural defects of the scanned surfaces.

9. The surface and sub-surface scanning apparatus of claim 8, wherein the computer generates an output format consistent with quantitative data related to a calculated percentage of structural defects and their respectively defined physical locations with respect to GPS standards in accordance with customer-defined specifications, the transportation industry, and/or respective governing body standards.

10. A method for evaluating surface and sub-surface conditions of underlying infrastructure, the method comprising the steps of providing, not necessarily in the order listed:

a vehicle-mounted high-definition visible band camera for capturing images of the surface to be evaluated;

a vehicle-mounted high-definition infrared band camera for sub-surface observation;

a detachable and adjustable structural boom assembly attached to a front, side or rear of the vehicle whereby the high-definition visible and infrared cameras are remotely mounted at a desired height vertically above the surface to be scanned so as to encompass a desired field of view (FOV), the FOV being preferably approximately at least one traffic lane in width or more of a portion of the structure to be evaluated;

an electronic laser range finder for measuring the height of the high-definition visible and infrared band cameras above the surface to be scanned;

at least one GPS antenna for real-time recording of vehicle position, speed, and direction with respect to actual latitude and longitude coordinates; and a computer for digitally processing measurements and video data signals collected by the high-definition visible and infrared band cameras.

11. The surface and sub-surface scanning apparatus of claim 5, further including at least one output monitor for displaying an output of the software such that an operator may visualize the internal structural condition of material below the surfaces scanned, thereby allowing the operator to identify and locate such structural defects and features apart from images from the visible band camera representing superficial, or nonstructural defects of the scanned surfaces.

* * * * *